(12) United States Patent
Aoyagi et al.

(10) Patent No.: US 6,324,896 B1
(45) Date of Patent: Dec. 4, 2001

(54) DESICCANT PACK WITH HUMIDITY SENSOR AND METHOD OF MANUFACTURING THE SAME

(75) Inventors: Yasutoshi Aoyagi, Taito-ku; Kazuo Watanabe, Kawasaki, both of (JP)

(73) Assignee: Fuji-Kagaku Kenkyujo Co., Ltd., Kanagawa (JP)

( * ) Notice: Subject to any disclaimer, the term of this patent is extended or adjusted under 35 U.S.C. 154(b) by 0 days.

(21) Appl. No.: 09/477,343

(22) Filed: Jan. 4, 2000

(30) Foreign Application Priority Data

Sep. 28, 1999 (JP) .................................... 11-273930

(51) Int. Cl.[7] ............... G01N 21/81; G01N 33/18; B01D 19/00
(52) U.S. Cl. .................. 73/29.01; 73/29.04; 73/31.01; 422/88; 340/602
(58) Field of Search ............... 73/29.01, 29.04, 73/29.02, 31.01, 31.05; 422/88; 340/602

(56) References Cited

U.S. PATENT DOCUMENTS

| | | | |
|---|---|---|---|
| 3,085,424 | * | 4/1963 | Berg ............................................ 73/53 |
| 3,776,038 | * | 12/1973 | Elliott ...................................... 73/335 |
| 4,641,524 | * | 2/1987 | Tarvin ...................................... 73/335 |
| 4,915,715 | * | 4/1990 | Oshima et al. .......................... 55/208 |
| 5,112,768 | * | 5/1992 | Carver ...................................... 436/39 |
| 5,161,085 | * | 11/1992 | Sakai et al. ........................... 361/286 |
| 5,419,177 | * | 5/1995 | Pastorello .............................. 73/23.4 |
| 5,834,626 | * | 11/1998 | De Castro et al. .................... 73/23.3 |
| 5,844,125 | * | 12/1998 | Pillion ................................ 73/29.01 |
| 5,855,849 | * | 1/1999 | Li et al. ................................... 422/88 |
| 6,049,680 | * | 4/2000 | Goris et al. ............................. 399/44 |
| 6,126,312 | * | 10/2000 | Sakai et al. ............................. 374/28 |
| 6,157,306 | * | 12/2000 | Mularoni ............................. 340/602 |

FOREIGN PATENT DOCUMENTS

463901 * 4/1975 (RU) .
WO 92/02804 * 2/1992 (WO) .

* cited by examiner

Primary Examiner—Helen Kwok
Assistant Examiner—David J. Wiggins
(74) Attorney, Agent, or Firm—Fildes & Outland, P.C.

(57) ABSTRACT

A desiccant pack 1 with a humidity sensor comprises a pack body 10 formed by sealing the three opened sides of a package film having gas permeability and heat sealability, and a desiccant is filled inside the pack body 10. Humidity sensor substances are applied in a band or strip-shape to the surface of the pack body 10, by which humidity sensors 21, 22 and 23 are applied directly to the pack.

6 Claims, 4 Drawing Sheets

DESICCANT PACK WITH HUMIDITY SENSOR AND METHOD OF MANUFACTURING THE SAME

FIELD OF THE INVENTION

The present invention relates to a desiccant pack with a humidity sensor, and the method of manufacturing the same.

DESCRIPTION OF THE PRIOR ART

Heretofore, it was common to enclose a pack having gas permeability filled with a desiccant to a package enwrapping food and the like, so as to reduce the humidity inside the package, and to prevent the quality of the packed goods such as food from deteriorating.

Recently, it has become common to enclose a desiccant pack to a plastic package having high sealability for conveying members such as electronic parts and electronic appliances, which are adversely affected by humidity.

It is necessary to control the humidity inside the package enwrapping electronic parts and the like, and therefore, it is required that the current humidity inside the package be detected.

In recent years, chemical substances are developed which change their color according to the humidity in the air. By applying the chemical substance onto a card and visually observing the change of its color, one is able to know the humidity of the air. A variety of chemical substances which react to different levels of humidity may be prepared. If the variety of chemical substances are applied in spots on one card, one is able to know the percentage of humidity in the air according to the color of the spots.

Such card is known as a humidity indicator card. The humidity indicator card may be enclosed together with the desiccant pack to a package enwrapping electronic parts and the like, so as to check the humidity of the air inside the package body.

SUMMARY OF THE INVENTION

According to the conventional method of enclosing the desiccant pack and the humidity indicator card to a package body, the pack and the card must be handled as a set, and it caused the rising of cost.

Therefore, the present invention aims at providing a desiccant pack with a humidity sensor integrated thereon and the corresponding manufacturing device of the integrated desiccant pack humidity sensor which solves the above-mentioned problems of the prior art.

The desiccant pack with a humidity sensor according to the present invention comprises, as a basic means, a pack body with one side portion being folded in upon itself along a lateral edge and other three sides being heat sealed along their lateral edges, a desiccant filled inside said pack body, and a humidity sensor substance being applied directly onto the surface of said pack body, which changes its color according to a varying ambient level of relative humidity. Further, the humidity sensor substance is applied in the shape of a band parallel to said side portion of the pack body being folded. Moreover, the humidity sensor substance includes a plurality of substances which react to different humidity levels respectively and change their color accordingly, said plurality of substances being applied in plural bands.

Next, the manufacturing device of the desiccant pack with a humidity sensor according to the invention comprises a package film manufacturing device including a supply roll for sending out a band-shaped package film base, and a humidity sensor application device for applying a liquid-state humidity sensor substance to the surface of a package film, and a pack manufacturing device connected to said package film manufacturing device, said pack manufacturing device including a center seal device for folding the supplied package film at the center portion in the width direction of said film and heat-sealing both side ends thereof, a hopper for measuring a desiccant and filling the same in said package film being center-sealed, an end seal device for heat-sealing the front and back ends of said package film, and a cutter for separating said heat-sealed package film to individual packs. Further, the humidity sensor application device comprises a plurality of humidity sensor units, each unit comprising a container storing said liquid-phase humidity sensor substance, an application roller to which said humidity sensor substance is adhered, and a backup roller opposing to said application roller, wherein said humidity sensor substance is applied onto the surface of said package film being conveyed between said application roller and said backup roller.

Moreover, the manufacturing device includes an air cylinder for driving said application roller to contact to or separate from said backup roller.

PREFERRED EMBODIMENT OF THE INVENTION

Figure 1:
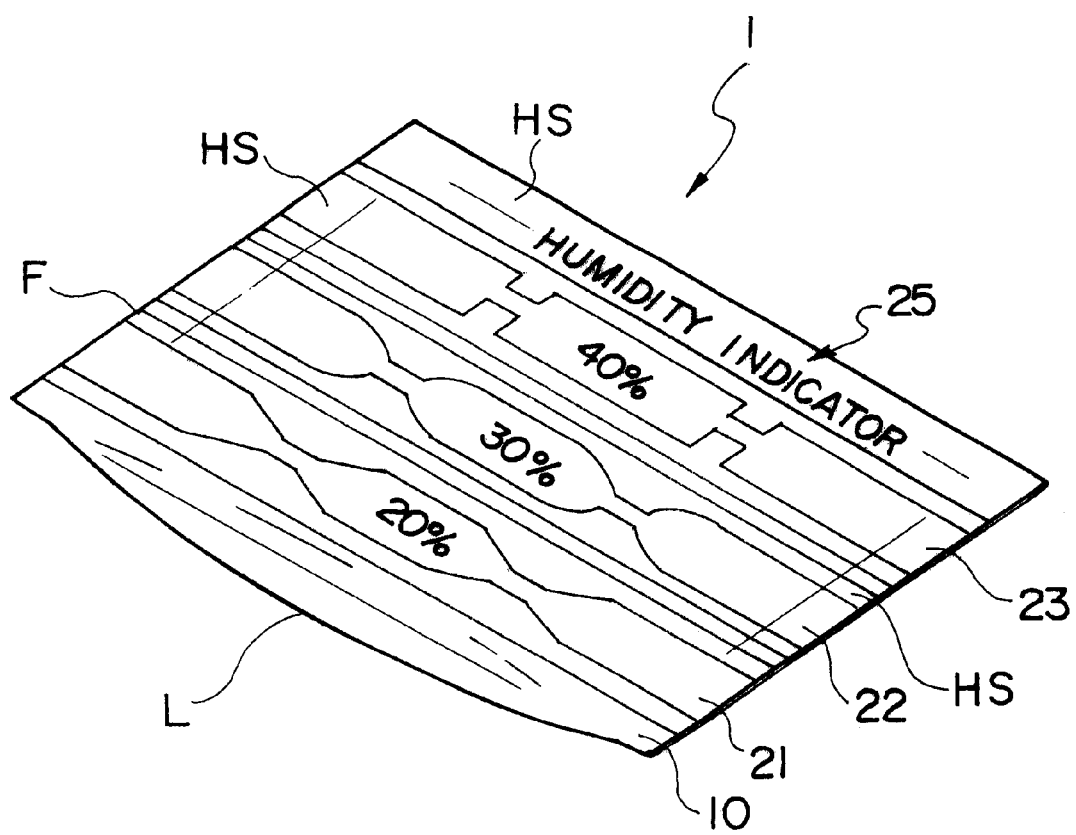
FIG. 1 is a perspective view of a desiccant pack with a humidity sensor according to the present invention.

FIG. 1 is a perspective view showing the appearance of a desiccant pack with a humidity sensor according to the present invention.

The desiccant pack with a humidity sensor shown as a whole by reference number 1 is manufactured by a manufacturing device explained later. A package film F having gas permeability is folded at its center in the width direction, and the three other side ends of the film are sealed by a heat seal HS, thereby forming a body 10.

A suitable desiccant (drying agent) is sealed inside the pack body 10. A generally used mineral such as a silica gel or a desicite and the like is used as the desiccant.

On the surface of the pack body 10 is equipped a first sensor portion 21 which reacts to a humidity of, for example, 20% and changes its color, a second sensor portion 22 which reacts to a humidity of 30%, and a third sensor portion 23 which reacts to a humidity of 40% and changes its color. Each sensor portion is formed by being printed onto the surface of the package film F. Further, an indication 25 notifying the user that the package is equipped with a humidity sensor is printed on the surface of the pack body 10.

A note indicating the type of the desiccant or a notice warning that the desiccant is not edible is printed on the back surface of the pack body 10.

Since a humidity sensor is directly printed on the surface of the body 10 of the desiccant pack 1, by merely sealing the desiccant pack in a package body for wrapping and protecting electronic parts and the like, the dehumidification of the package in which electronic parts are packed and the indication of the interior humidity of the package may be achieved by a single desiccant pack. Accordingly, the present invention provides a desiccant pack which is easy to handle, and which contributes to cut down the cost of a package.

Figure 2:
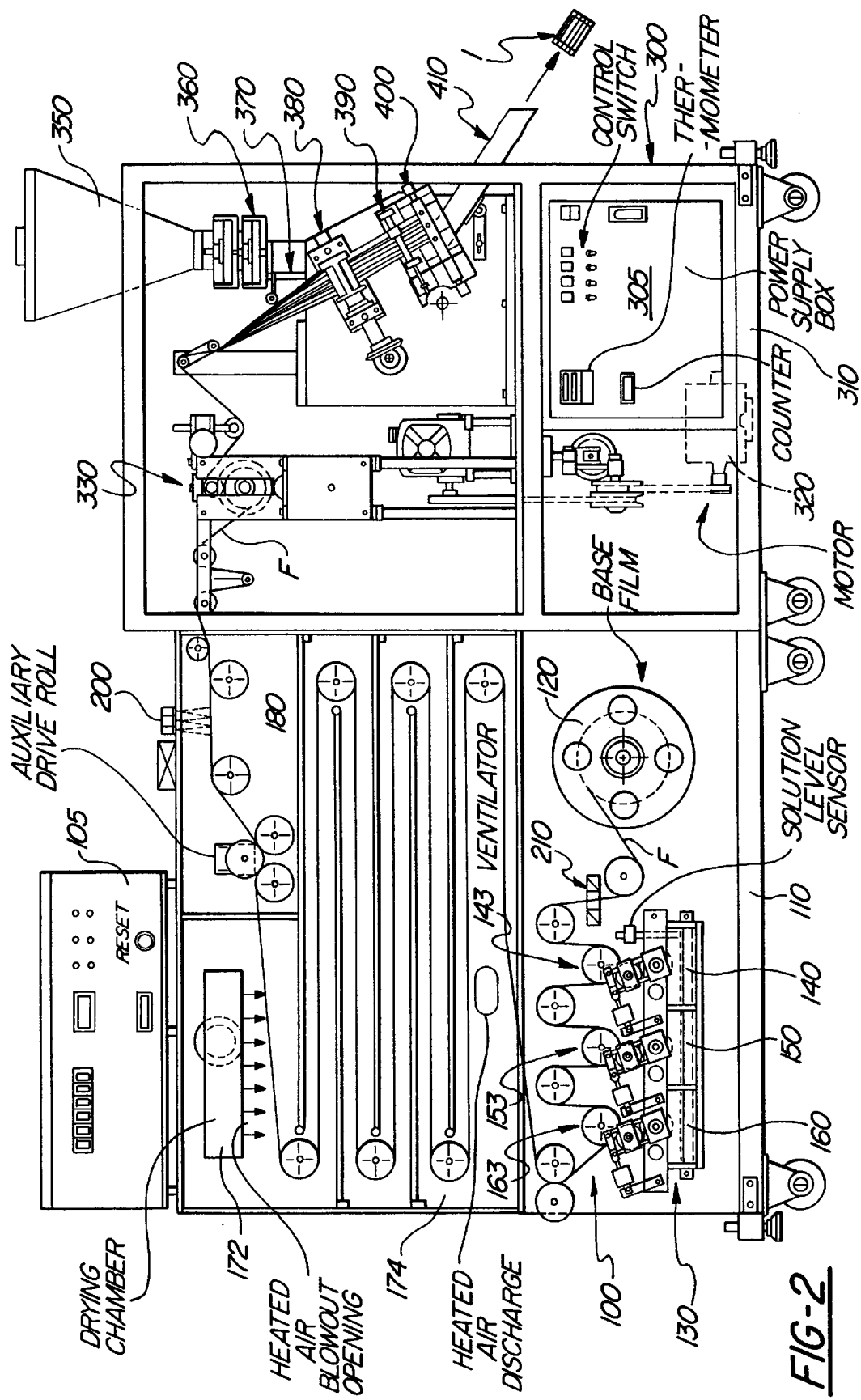
FIG. 2 is a front view of a manufacturing device of the desiccant pack with a humidity sensor according to the present invention.
Figure 3:
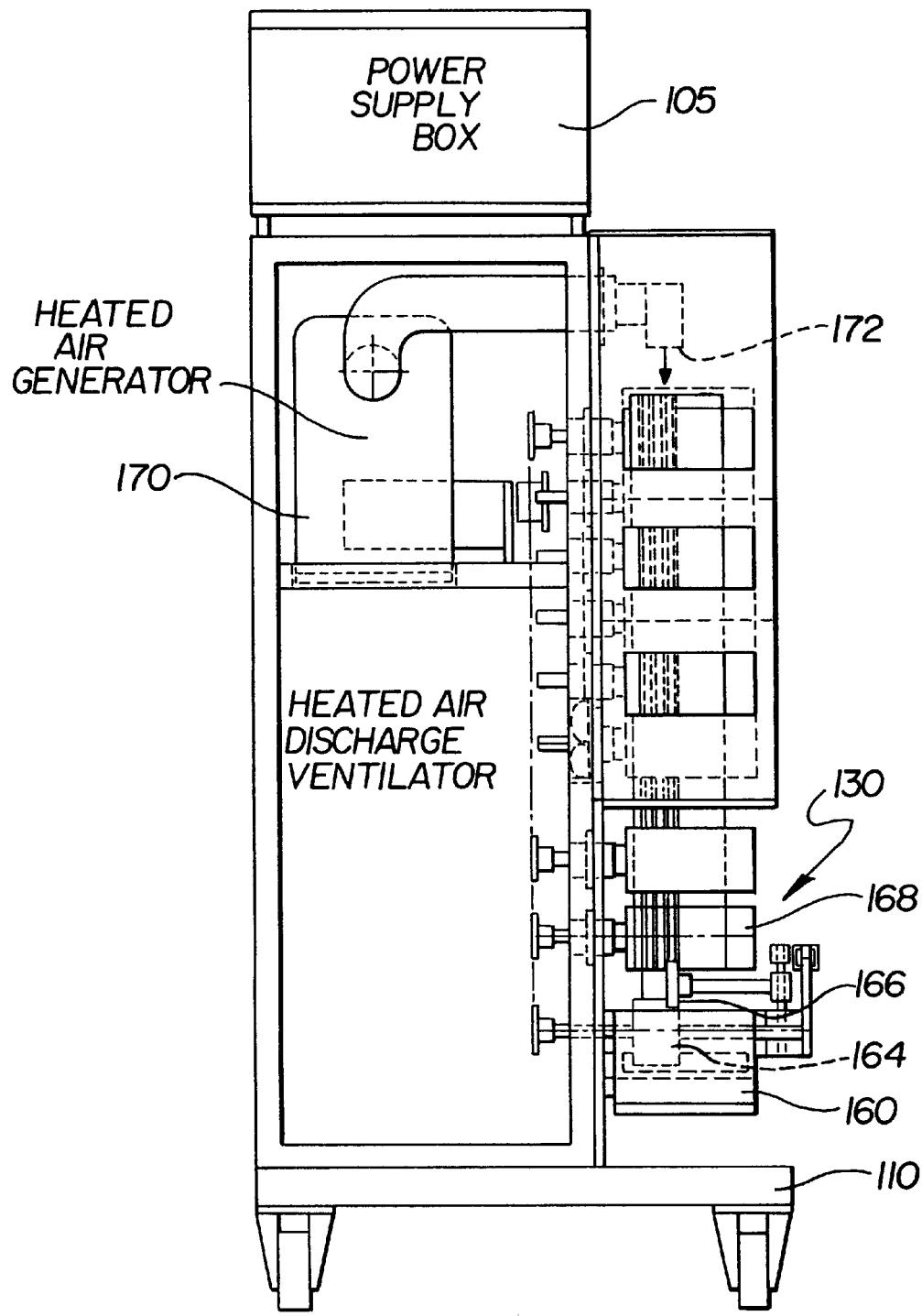
FIG. 3 is a left side view of the manufacturing device of the desiccant pack with a humidity sensor according to the present invention.
Figure 4:
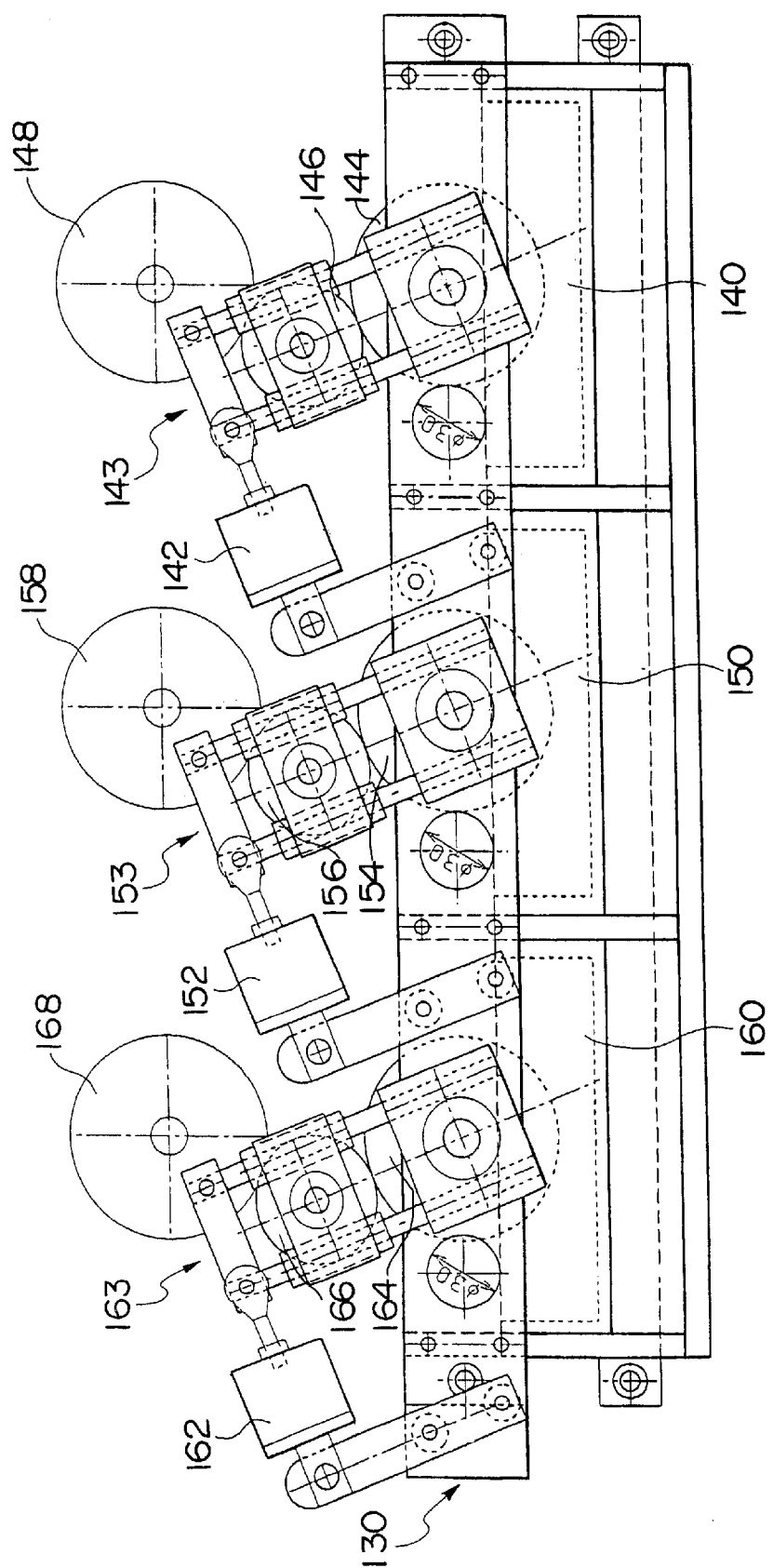
FIG. 4 is a front view showing the main portion of the manufacturing device of the desiccant pack with a humidity sensor according to the present invention.

FIG. 2 is a front view of a manufacturing device of the desiccant pack with a humidity sensor according to the present invention, FIG. 3 is a left side view of FIG. 2, and FIG. 4 is a front view of the main portion of FIG. 2.

The manufacturing device of the present invention is structured by connecting in series a manufacturing device 100 of a package film for forming a desiccant pack and a packaging device 300 of a desiccant pack utilizing the package film.

The package film manufacturing device 100 comprises a power equipped to the upper portion of a frame 110 and a control panel 105.

The frame 110 comprises a supply reel 120 of a base film, from which the package film F is pulled out.

The package film F is a film having gas permeability and heat sealability to which necessary letter patterns are printed in advance, which is guided through various rollers equipped to the frame 110 to an application device 130 for applying a humidity sensor substance.

FIG. 4 shows the details of the humidity sensor application device 130 comprising three containers 140, 150 and 160 each storing a liquid-state sensor substance.

Liquid-state humidity sensor substances which change color reacting to humidity of different percentages respectively is stored in each container. According to the present embodiment, a substance for sensing a humidity of 40% is stored in the first container 140, a substance for sensing a humidity of 30% is stored in the second container 150, and a substance for sensing a humidity of 20% is stored in the third container 160.

The number of containers to be equipped to the device or the percentage of humidity being sensed may be selected appropriately according to need.

An application unit 143 for applying the sensor substance is mounted to the first container 140. The unit 143 comprises a roller 144 which comes into contact with the sensor substance, and an application roller 146. A package film F is sandwiched between the application roller 146 and a backup roller 148. The application roller 146 is moved by an air cylinder 142 to contact to or separate from the backup roller 148. Application units 153, 163 of the same kind for applying the humidity sensor substances are each equipped to the second container 150 and the third container 160, respectively.

As shown in FIG. 3, application rollers 146, 156 and 166 of the three sets of application units are placed so that their position in the width direction of the package film F differ. The application rollers apply the humidity sensor substances in a band or strip-shape along a predetermined position in the width direction of the package film F and in the direction that the package film F travels.

The package film F, to which the humidity sensor substances are applied in a predetermined position, is sent to a drying chamber 174. A heated current of air which is generated in a heated air generator 170 is blown out from a blowout opening 172. By the heated air, the humidity sensor substances applied on the package film F are dried.

A drive roll 180 operates to grip and transmit the package film F. Since the dried humidity sensor substances have a unique color tone, the application state and the dryness of the humidity sensor substances are checked by a distinction sensor 200. The completed package film F is sent to a packaging device 300.

The packaging device 300 comprises a power and a control panel 305 positioned inside a frame 310, and a motor 320 for driving each mechanism.

The package film F supplied from the manufacturing device of the package film is printed of necessary notes and marks in advance. Therefore, a print position adjusting device 330 is used to adjust the printed position in the longitudinal direction of the package film F. The package film F completed of the positioning of the printing is sent to a three-side sealing device.

The three-side sealing device is formed so as to fold the package film at the width-direction center of the film, apply a center seal thereto so as to form a cylinder-shaped film, fill a predetermined amount of desiccant in the cylindrical film, and seal the opened front and back side ends of the film (end-seal), thereby manufacturing a pack.

The desiccant is placed inside a material tank 350, divided into predetermined amounts by a measurement device 360, and filled through a hopper 370 to the cylindrical package film. The package film, provided of the center seal and the end seal between the heat roll 380 and the pull roll 390, is then separated to individual packs by a rotary cutter 400, and discharged from a chute 410 as a desiccant pack with a humidity sensor 1 explained with reference to FIG. 1.

The desiccant pack with a humidity sensor according to the present invention is formed by directly printing a humidity sensor onto the surface of a pack filled with a desiccant. Therefore, merely by placing the desiccant pack alone into a package body, the internal humidity of the package body may be indicated and the dehumidification of the package body may be performed at the same time. Accordingly, the electronic parts and the like which is packed inside the package body is protected from humidity, and the quality of the packed goods during distribution is secured.

Moreover, the manufacturing device of the desiccant pack with a humidity sensor characterizes in preparing a base paper of a package film of the desiccant pack in a roll-like shape, applying the liquid-type humidity sensor substance automatically to the surface of the base paper, drying the substance and then sending the film out to a three-side seal device, sealing the three opened sides of the package film, and then automatically filling a predetermined amount of desiccant inside the film.

By using the device, the desiccant pack with a humidity sensor according to the invention may be manufactured automatically.

We claim:

1. A desiccant pack with a humidity sensor comprising:
   a pack body having a set of sides and corresponding edges arranged about a pack body inner surface and outer surface, each side formed by a row of two or more side portions, with one side having a portion being folded in upon itself along a lateral edge and with the other remaining sides being heat sealed along their lateral edges;
   a desiccant filled inside the inner surface on said pack body; and a humidity sensor substance being applied directly onto the outer surface of said pack body, which substance manifests an observable moisture sensitive reaction and changes its color according to a varying ambient level of relative humidity.

2. A desiccant pack with a humidity sensor defined in claim 1, wherein said humidity sensor substance is applied in the shape of a band parallel to said side portion of the pack body being folded.

3. A desiccant pack with a humidity sensor defined in claim 2, wherein said humidity sensor substance includes a plurality of substances which react to different humidity levels respectively and change their color accordingly, said plurality of substances being applied in plural bands.

4. A manufacturing device of a desiccant pack with a humidity sensor comprising:

a package film manufacturing device including a supply roll for sending out a band-shaped package film base, and a humidity sensor application device for applying a liquid-state humidity sensor substance to the surface of a package film; and a pack manufacturing device connected to said package film manufacturing device, said pack manufacturing device including a center seal device for folding the supplied package film at the center portion in the width direction of said film and heat-sealing both side ends thereof, a hopper for measuring a desiccant and filling the same in said package film being center-sealed, an end seal device for heat-sealing the front and back side ends of said package film, and a cutter for separating said heat-sealed package film to individual packs.

5. A manufacturing device of a desiccant pack with a humidity sensor defined in claim 4, wherein said humidity sensor application device comprises a plurality of humidity sensor units, each unit comprising a container storing said liquid-state humidity sensor substance, an application roller to which said humidity sensor substance is adhered, and a backup roller opposing to said application roller, wherein said humidity sensor substance is applied onto the surface of said package film being conveyed between said application roller and said backup roller.

6. A manufacturing device of a desiccant pack with a humidity sensor defined in claim 5, wherein said manufacturing device includes an air cylinder for driving said application roller to contact to or separate from said backup roller.

* * * * *